(12) United States Patent
Holmström et al.

(10) Patent No.: US 8,244,337 B2
(45) Date of Patent: Aug. 14, 2012

(54) METHOD AND IMPLANTABLE MEDICAL DEVICE FOR CLASSIFYING SENSOR SIGNALS

(75) Inventors: Nils Holmström, Järfälla (SE); Malin Öhlander, Stockholm (SE)

(73) Assignee: St. Jude Medical AB, Jarfalla (SE)

( * ) Notice: Subject to any disclaimer, the term of this patent is extended or adjusted under 35 U.S.C. 154(b) by 903 days.

(21) Appl. No.: 12/280,505

(22) PCT Filed: Feb. 28, 2006

(86) PCT No.: PCT/SE2006/000264
§ 371 (c)(1),
(2), (4) Date: Dec. 23, 2008

(87) PCT Pub. No.: WO2007/100276
PCT Pub. Date: Sep. 7, 2007

(65) Prior Publication Data
US 2009/0099614 A1    Apr. 16, 2009

(51) Int. Cl.
*A61B 5/04* (2006.01)

(52) U.S. Cl. ........................................... 600/513

(58) Field of Classification Search ............... 600/513, 600/301; 607/4, 9, 14, 17, 28
See application file for complete search history.

(56) References Cited

U.S. PATENT DOCUMENTS

| | | |
|---|---|---|
| 6,490,486 B1 | 12/2002 | Bradley |
| 6,879,861 B2 | 4/2005 | Benz et al. |
| 2003/0083711 A1 | 5/2003 | Yonce et al. |
| 2003/0199957 A1 | 10/2003 | Struble et al. |
| 2004/0078058 A1 | 4/2004 | Holmstrom et al. |
| 2004/0138717 A1 | 7/2004 | Strandberg |
| 2005/0131476 A1 | 6/2005 | Kim et al. |
| 2007/0142866 A1* | 6/2007 | Li et al. ................... 607/17 |
| 2011/0160551 A1* | 6/2011 | Li et al. ................... 600/301 |

* cited by examiner

*Primary Examiner* — George Manuel
*Assistant Examiner* — Robert N Wieland

(57) ABSTRACT

In a method and an apparatus for creating hemodynamic sensor signal templates using an implantable medical device connectable to a patient heart activity of the patient is sensed in order to identify a paste or sensed sequence of events of a heart cycle. Hemodynamic sensor signals for consecutive heart cycles are sensed and the sensed hemodynamic sensor signals for consecutive heart cycles are stored. The sensed sensor signals are classified dependent on at least one predetermined heart event sequence condition. A template may be created using the classified sensor signals.

50 Claims, 9 Drawing Sheets

METHOD AND IMPLANTABLE MEDICAL DEVICE FOR CLASSIFYING SENSOR SIGNALS

BACKGROUND OF THE INVENTION

1. Field of the Invention

The present invention generally relates to implantable medical devices, such as cardiac pacemakers and implantable cardioverter/defibrillators, and in particular to an improved method and medical device for automatically classifying hemodynamic sensor signals.

2. Description of the Prior Art

Today, in the modern society, heart diseases and/or conditions leading to an impaired heart function are a major problem entailing constantly increasing costs for medical services. For example, heart failure is a condition which affects thousands of people throughout the world. Congestive heart failure (CHF) is an ability of the heart to pump blood at an adequate rate in response to the filling pressure. Patients suffering from CHF are often afflicted by cardiogenic pulmonary edema, which is caused by the accumulation of fluid in the lung interstitium and alveoli due to the fact the left ventricular venous return exceeds left ventricular cardiac output. That is, more fluids are transported to the lung region than from the lung region causing the accumulation of fluids in the lung region. CHF may even, in its more severe stages, result in death.

Accordingly, reliable and accurate information, e.g. obtained by means of hemodynamic sensors implanted in the body of a patient, regarding the cardiac function of a patient is of a high value, for example, in order to detect CHF on an early stage or to trend a progression of CHF of a patient. These sensors may include sensors for sensing a blood pressure of the patient or sensing the electrical bio-impedance of the patient. The sensor signals reflects the contraction of the heart, which is highly dependant on whether the patient is paced or not and also the sequence and timings with which the patient is being paced.

One obvious way of increasing the accuracy of the sensor signals is to collect the signals for a number of heartbeats and make a template or reference of the sensor signal representing an average of the heart cycles. Each template hence represents a number of cardiac waveform morphologies. Thereby, influence from noise can be reduced and effects of respiration can be smoothened out. However, when creating such a template from a number of sensor signals for a number of heart cycles it is a great importance that heart cycles that are included into the creation of the template have the same sequence pattern, i.e. the same paced or sensed sequence of heart events. It is also of importance that the starting points of recording the heart beats are the same event in the heart cycle, e.g. a P-wave, R-wave in the right or left ventricle or a pacing pulse in one of the heart chambers.

United States Patent Application Publication No. 2004/0243014 discloses a method and system for creating and maintaining such cardiac waveform templates. A cardiac waveform is formed by identifying one or more cardiac waveform features representative of a particular cardiac beat morphology including morphological features such as curvature, inflection points, rise or fall times, slopes, or the like. Targets regions associated with the identified cardiac waveform features are defined and used to establish a template representing a particular waveform morphology, such as a normally conducted cardiac rhythm. This method thus requires extensive signal processing in order to identify the morphological features such as curvature, inflection points, rise or fall times, slopes, or the like.

United States Patent Application Publication No. 2003/0181818 discloses a method and system for generating a snapshot representative of one beat of a patient's supraventricular rhythm. A number of templates are provided and selectively updated with qualified beats and are used to characterize the patient's supraventricular rhythm.

Accordingly, there is a need of an improved method and medical device for automatically classifying or qualifying hemodynamic sensor signals and for creating hemodynamic sensor signal templates.

SUMMARY OF THE INVENTION

Thus, an object of the present invention is to provide an improved method and medical device for automatically classifying hemodynamic sensor signals.

Another object of the present invention is to provide an improved method and medical device for automatically creating hemodynamic sensor signal templates.

In the context of this application, the term "impedance" refers to the low frequency component of the impedance. The impedance is calculated as $z=u/i$, where u is the measured voltage and i is the applied excitation current.

Moreover, in order to clarify, the term "cardiogenic impedance" is defined as the impedance or resistance variation that origins from cardiac contractions or, in other words, the cardiac component of the impedance measured between electrodes of the medical device including the case of the device.

In this application the term "contraction pattern" refers to the sequence of events of consecutive heart cycles of a heart.

According to an aspect of the present invention, there is provided a method for classifying hemodynamic sensor signals using an implantable medical device being connectable to a patient. The method comprises the steps of performing a data collection session for collecting hemodynamic sensor signals for consecutive heart cycles including: sensing a heart activity of a patient in order to identify a paced or sensed sequence of events of a heart cycle; sensing hemodynamic sensor signals for consecutive heart cycles; storing said sensed hemodynamic sensor signals for consecutive heart cycles; and classifying sensed sensor signals on basis of at least one predetermined heart event sequence condition.

According to a second aspect of the present invention, there is provided a medical device for classifying hemodynamic sensor signals being connectable to a patient. The device comprises a heart activity sensor adapted to sense a heart activity of a patient; a hemodynamic sensor adapted to sense hemodynamic signals for consecutive heart cycles; a storage adapted to store the sensed hemodynamic sensor signals for consecutive heart cycles; a processing unit adapted to: perform a data collection session for collecting hemodynamic sensor signals for consecutive heart cycles including: to obtain paced or sensed sequence of events of heart cycles from the heart activity sensor; to trigger the hemodynamic sensor to initiate a sensing session in order to sense hemodynamic sensor signals for consecutive heart cycles; and to store the sensed hemodynamic sensor signals for consecutive heart cycles in the storage; and wherein the processing unit is adapted to classify sensed sensor signals on basis of at least one predetermined heart event sequence condition.

According to a third aspect of the present invention, there is provided a computer program product, which when executed on a computer, performs steps in accordance with the first aspect of the present invention.

According to a further aspect of the present invention, there is provided a computer readable medium comprising instructions for bringing a computer to perform a method according to the first aspect of the present invention.

Thus, the invention is based on classifying hemodynamic sensor signals collected over several heart cycles on basis of at least one predetermined heart event sequence condition. For example, the heart beats can be grouped according to their heart event sequence patterns. Thereby, it can be assured that each heart cycle in a group has substantially the same heart event sequence pattern and that the starting points of the recording of each heart beat is the same event in the heart cycle, e.g. a P-wave, R-wave in the right or left ventricle or a pacing pulse in one of the heart chambers.

In one embodiment, sensor signals for heart cycles that has a paced or sensed sequence of events that satisfies the at least one predetermined heart event sequence condition is selected. This selected heart beats can be used to, for example, assess the cardiac function of the patient.

According to one embodiment, the selected heart beats are used to create a template. It can be assured that the template is reliable and represents a certain heart event sequence pattern. Such a template is of great use. For example, it can be used to assess the cardiac function of a patient by using the signal morphology of the template. By assuring that each included heart cycle has substantially the same heart event sequence pattern it can be avoided that the template represents a mishmash of various heart event sequence patterns. Each template is accordingly created of hemodynamic sensor signals over several heart cycles. For example, by averaging or by median filtering, the signals. Thereby, noise can be reduced and effects from, for example, respiration can be smoothened out.

In another embodiment, a predetermined parameter in the consecutive sensor signals is identified or extracted, for example, the contractility or the end-diastolic volume. Thereby, it is possible to, for example, trend changes over time of the identified parameter.

In one embodiment the selected sensor signals for heart cycles, i.e. the paced or sensed sequences of events that satisfies the at least one predetermined heart event sequence condition is transferred to an external unit, for example, a programming unit via a communication link, for example, a telemetry link. The template may then be created in the external programming unit.

According to an embodiment of the present invention, the at least one predetermined heart event sequence condition includes a reference sequence. This reference sequence may be a pre-programmed sequence stored in the processing unit or the storage. A physician may change this predetermined sequence, for example, by programming a new sequence using an external programming unit and transferring the new sequence to the device via a telemetry link. Alternatively, the algorithm may be set to collect data at any paced/sensed sequence. To determine which sequence to use, the algorithm may count the prevalence of the sequence occurring during a predetermined interval and use the most prevalent to create the template.

In another embodiment of the present invention, it is determined whether a series of paced or sensed sequences of events is stable and, if the series is found to be stable, the data collection session to collect hemodynamic sensor signal the template is initiated. That is, it is verified that the cardiac contraction pattern is stable enough to collect data for the template. According to one embodiment, if the reference sequence is predetermined, the algorithm registers the heart cycles (i.e. the sequence events of the consecutive heart cycles) to verify that the sequences corresponding to the reference sequence exceeds a predetermined limit, for example, a percentage of the heart cycles occurring during the interval. If the paced or sensed sequences corresponding to the reference sequence exceeds the predetermined limit, the data collection session is initiated. To elaborate, the following steps are performed: sensing a heart activity of a patient during a predetermined period of time; checking whether a prevalence of a paced or sensed sequence of events of consecutive heart cycles that corresponds to the reference sequence satisfies at least one predetermined condition; and, if said at least one predetermined condition is found to be satisfied, determining that said series of paced or sensed sequences of events of said patient is stable. In addition the step of checking whether at least a predetermined percentage of the sequences of events of the heart cycles occurring during the predetermined period of time corresponds to said reference sequence may be executed. According to another embodiment, if the algorithm is set to collect data at any paced/sensed sequence, the prevalence of the sequences occurring during the predetermined interval and the most prevalent is used to create the template. To ensure that the sequence pattern is stable enough, a minimal level of the prevalence of the paced/sensed sequence may be set. A further embodiment is to count the prevalence of the individual events, i.e. atrial, right and left ventricular sensed/paced events, and use a sequence containing the most prevalent events.

According to a further embodiment of the present invention, the paced or sensed sequences of heart cycles that is found not to correspond to the reference sequence is counted during the data collection session; and the data collection session is aborted if the paced or sensed sequences of heart cycles that is found not to correspond to the reference sequence exceeds a predetermined abortion condition. The abort condition may be a predetermined percentage. Another abort condition may be that a predetermined number of sequences corresponding to the reference sequence has not been obtained during a predetermined period of time.

In a further embodiment of the present invention, the hemodynamic sensor signals are the cardiac component of an electrical bio-impedance of the patient. In an embodiment, an excitation current pulse is applied between at least a first electrode and at least a second electrode; the impedance in tissues between the electrodes to the excitation current pulse is sensed, and the cardiac component of said sensed impedance is extracted. The sensed signal often contains elements originating from both the cardiac cycle and the respiratory cycle. With appropriate electrode configuration and filtering the cardiac component of the impedance signal can be separated from the respiratory component and used for cardiogenic impedance algorithms. According to alternative embodiments, the hemodynamic sensor signals are a blood pressure of the patient or a blood flow of the patient.

In alternative embodiments of the present invention, it is checked whether at least one predetermined start criteria is fulfilled. In a first embodiment, a heart rate of the patient is sensed, it is checked whether said sensed heart rate satisfies at least one predetermined condition, for example, within a predetermined interval; and, if said sensed heart rate is found to satisfy said at least one condition, the data collection session is initiated. In another embodiment, an activity level of the patient is sensed, it is checked whether said sensed activity level satisfies at least one predetermined condition, for example, within a predetermined interval; and, if the sensed activity level is found to satisfy the at least one condition, the data collection session is initiated. In yet another embodiment of the present invention, at least one body position of the patient is detected; and the data collection session is initiated when said patient is in the at least one body position. According to a further embodiment of the present invention, a breath rate of the patient is sensed, it is checked whether said sensed breath rate satisfies at least one predetermined condition, for example, within a predetermined interval, and, if said sensed breath rate is found to satisfy said at least one condition, the data collection session is initiated.

According to further embodiments, the template may be created by averaging the hemodynamic sensor signals, by median filtering the hemodynamic sensor signals, by combinations of averaging the hemodynamic sensor signals and median filtering the hemodynamic sensor signals, or by weighting the hemodynamic sensor signal for different heart cycles with predetermined and different weights.

As will be apparent to those skilled in the art, the methods of the present invention, as well as preferred embodiments thereof, are suitable to realize as a computer program or a computer readable medium.

BRIEF DESCRIPTION OF THE DRAWINGS

The features that characterize the invention, both as to organization and to method of operation, together with further objects and advantages thereof, will be better understood from the following description used in conjunction with the accompanying drawings. It is to be expressly understood that the drawings is for the purpose of illustration and description and is not intended as a definition of the limits of the invention. These and other objects attained, and advantages offered, by the present invention will become more fully apparent as the description that now follows is read in conjunction with the accompanying drawings.

DESCRIPTION OF THE PREFERRED EMBODIMENTS

Figure 1:
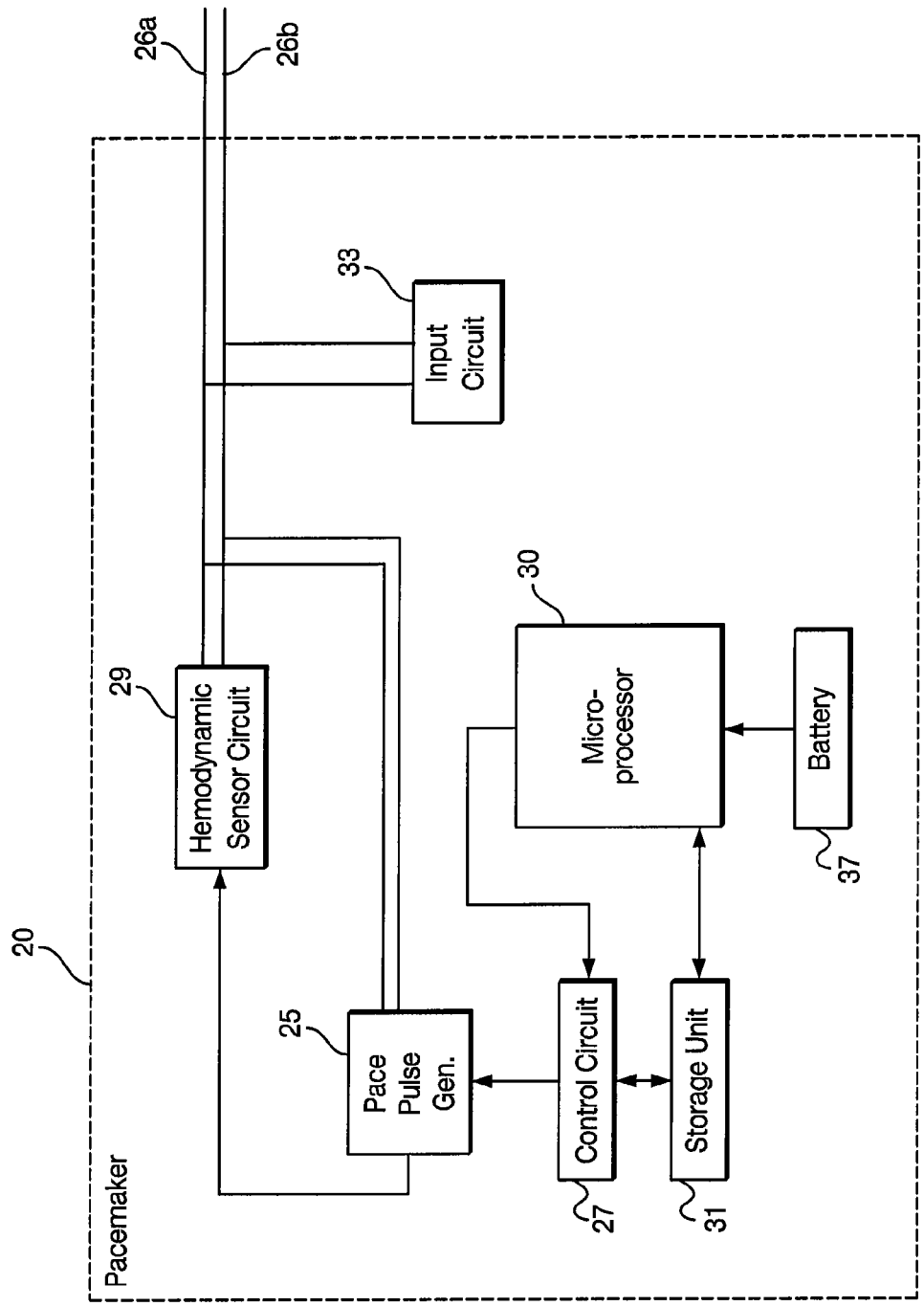
FIG. 1 is block diagram of the primary functional components of a first embodiment of an implantable medical device in accordance with the present invention.

With reference first to FIG. 1, the configuration including the primary functional components of a first embodiment of an implantable medical device in accordance with the present invention will be described. In the following, the present invention will be described in the context of a pacemaker. However, as the man skilled within the art easily realizes, the present invention may also be implemented with in the contents of, for example, an implantable cardioverter/defibrillator.

The illustrated embodiment comprises an implantable medical device 20, such as a pacemaker. The pacemaker 20 has a housing that is hermetically sealed and biologically inert. Normally, the housing is conductive and may, thus, serve as an electrode. One or more pacemaker leads, where only two are shown in FIG. 1, namely a ventricular lead 26a and an atrial lead 26b, are electrically coupled to the pacemaker 20 in a conventional manner. The leads 26a, 26b extend into the heart (not shown) via a vein of the patient. One or more conductive electrodes for receiving electrical cardiac signals and/or for delivering electrical pacing to the heart may be arranged near the distal ends of the leads 26a, 26b.

The leads 26a, 26b may be unipolar or bipolar, and may include any of the passive or active fixation means known in the art for fixation of the lead to the cardiac tissue. As an example, the lead distal tip (not shown) may include a tined tip or a fixation helix. The leads 26a, 26b have one or more electrodes (as described with reference to FIG. 1), such a tip electrode or a ring electrode, arranged to, inter alia, transmit pacing pulses for causing depolarization of cardiac tissue adjacent to the electrode(-s) generated by a pace pulse generator 25 under influence of a control circuit 27. The control circuit 27 controls pace pulse parameters such as output voltage and pulse duration.

Moreover, an hemodynamic sensor circuit 29 is adapted to sense hemodynamis sensor signals. In one embodiment, the hemodynamic sensor circuit 29 is an impedance circuit adapted to carry out impedance measurements. The impedance circuit 29 is arranged to apply excitation current pulses between a first electrode and second electrode adapted to positioned, for example, within a heart of the patient in an embodiment where the cardiogenic impedance is measured. The impedance circuit 29 is also arranged to sense the impedance in the tissues between the first and second electrode to the excitation current pulse. Further, the impedance circuit 29 is coupled to a processing unit, for example, a microprocessor 30, where, inter alia, processing of the obtained impedance signals can be performed. In an embodiment where the cardiac component of the electrical bio-impedance is sensed, the impedance circuit 29 is arranged to apply an excitation current pulse between a first electrode and a second electrode arranged to be positioned at different position within the heart of the patient and to sense the impedance in the tissues between the first and second electrode to the excitation current pulse. As an example the excitation current may be applied between the case (or housing) and a RV-coil (i.e. the conductor in a bipolar lead having a helical configuration located in the right ventricle), and the voltage may be sensed between the case and the RV-coil. In a further example, the excitation current may be applied between the RV-coil and a RA-tip (i.e. the distal electrode in a bipolar lead located in right atrium) and the voltage may be sensed between the RV-coil and a RA-ring (i.e. the proximal electrode in a bipolar lead located in right atrium). Of course, as the skilled man realizes, there are other conceivable configurations that can be used. The microprocessor 30 may be arranged to extract the cardiac component of the sensed impedance. In other embodiments of the present invention, the hemodynamic sensor circuit may be, for example, a blood pressure sensor, or a blood flow sensor.

The impedance sensing circuit 29 is controlled by the microprocessor 30 and the control circuit 27. The control circuit 27 acts under influence of the microprocessor 30. A storage unit 31 is connected to the control circuit 27 and the microprocessor 30, which storage unit 31 may include a random access memory (RAM) and/or a non-volatile memory such as a read-only memory (ROM). Detected signals from the patient's heart are processed in an input circuit 33 and are forwarded to the microprocessor 30 for use in logic timing determination in known manner. In particular, the input circuit 33 is connected to cardiogenic sensors located in the lead 26a and/or 26b adapted to sense events of the heart cycles of the patient, such as a P-wave, an R-wave in the right or left ventricle or a pacing pulse in one of the heart chambers.

The implantable medical device 20 is powered by a battery 37, which supplies electrical power to all electrical active components of the medical device 20. Data contained in the storage unit 31 can be transferred to a programmer (not shown) via a programmer interface (not shown). For example, the created template can be transferred for assessment of the cardiac function.

Figure 2A:
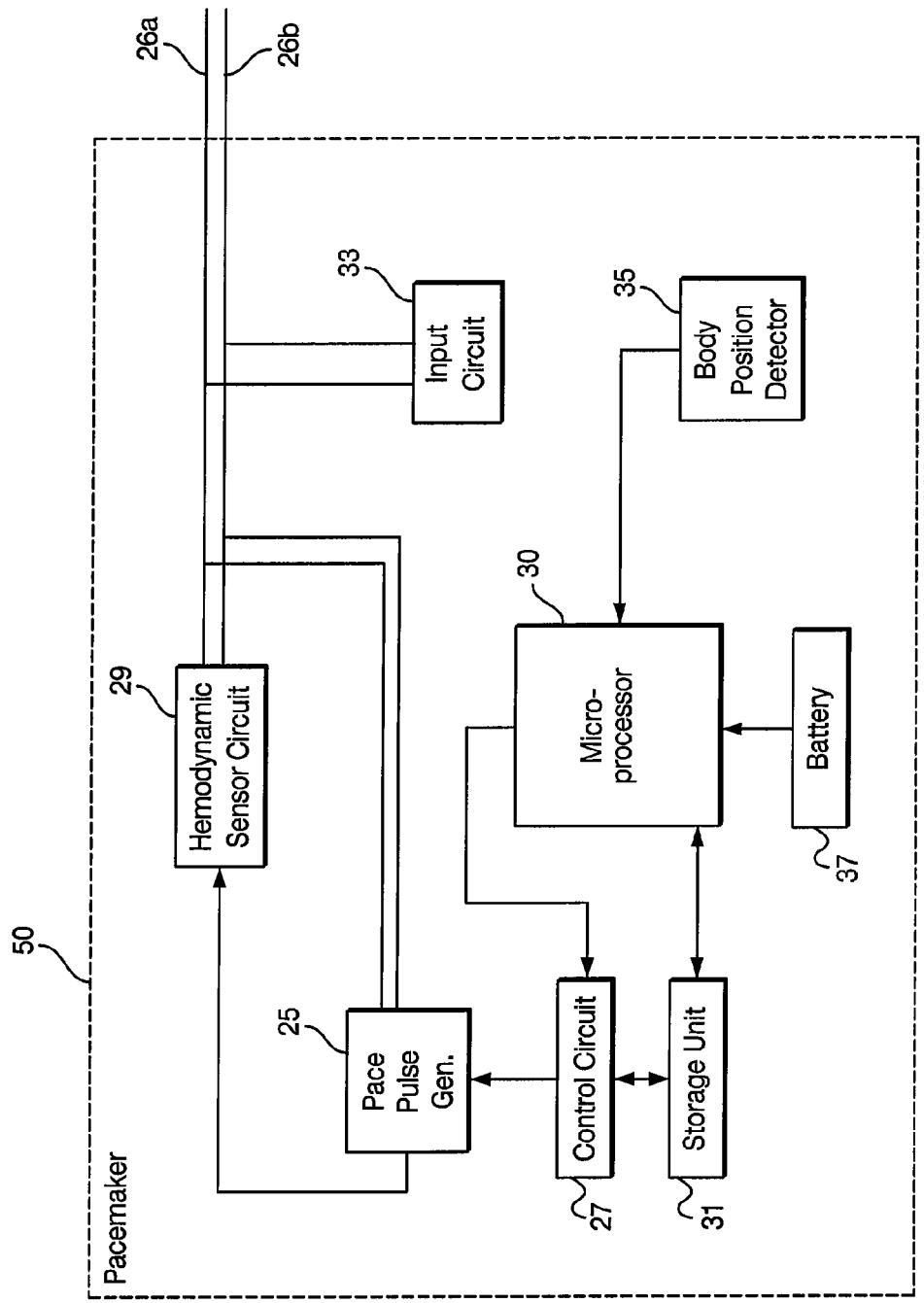
FIG. 2a is block diagram of the primary functional components of a second embodiment of an implantable medical device in accordance with the present invention.

With reference now to FIGS. 2a-2d, embodiments of the present invention will be discussed. In FIGS. 1 and 2a-2d similar parts are denoted with the same reference numerals. Turning first to FIG. 2a, an embodiment of an implantable medical device according to the present invention will be discussed. The implantable medical device 50 according to the present invention has a position detecting sensor 35 arranged to detect a predetermined, specific body position of the patient. In one embodiment of the present invention, the position detecting means is a back-position sensor arranged to sense when the patient is lying on his or her back (or on his or her face). The position detecting sensor 35 is connected to the microprocessor 30. In one embodiment, a data collection session is initiated in order to collect hemodynamic sensor signals for use in the creation of a template when the patient is in a specific body position. Accordingly, the body position of the patient can be used as a start criteria for the algorithm. The position detecting sensor can be incorporated in the device in accordance with conventional practice within the art. Of course, there are other conceivable positions, for example, right or left or prone.

Figure 2B:
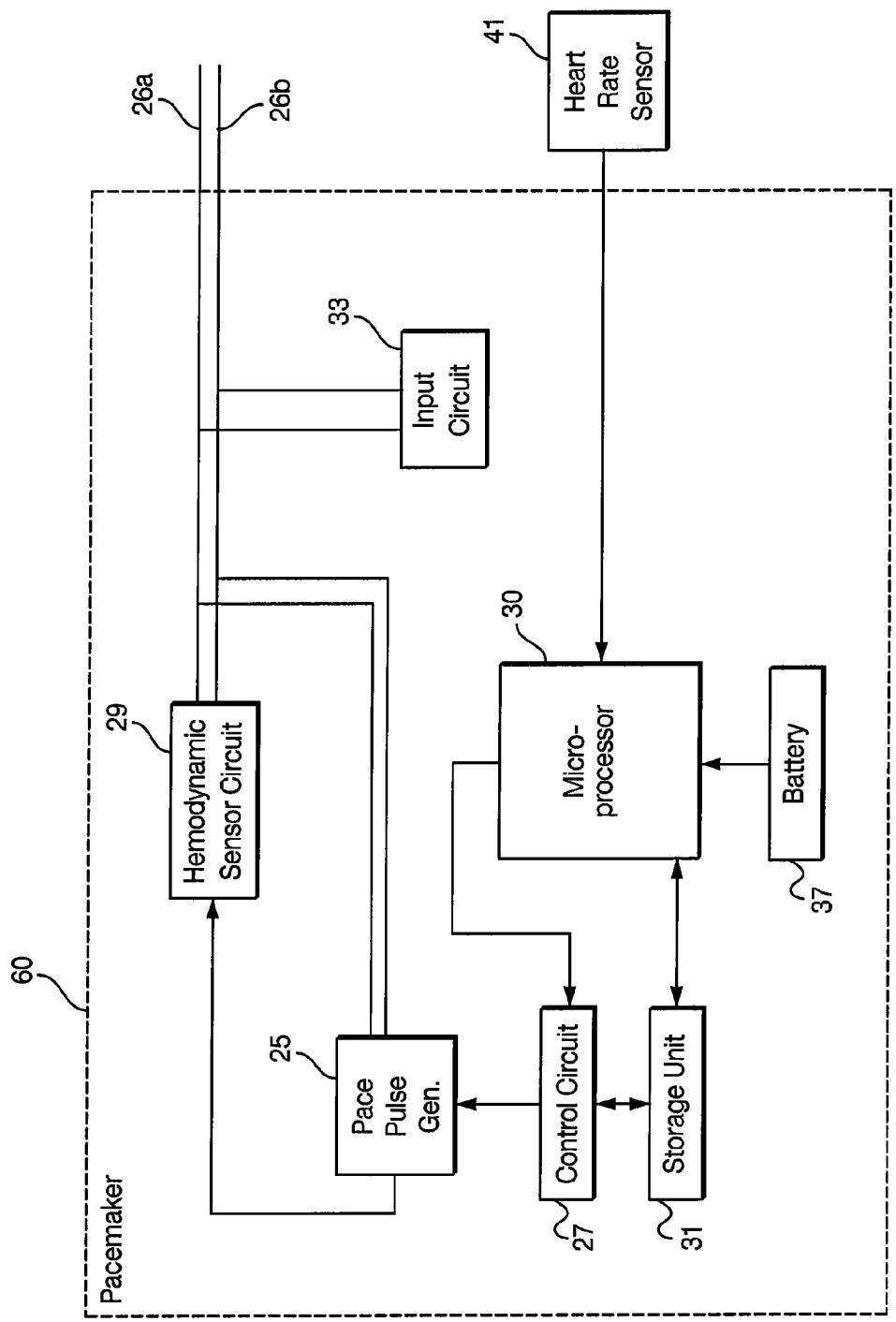
FIG. 2b is block diagram of the primary functional components of a third embodiment of an implantable medical device in accordance with the present invention.

Referring now to FIG. 2b, a further embodiment will be discussed. According to this embodiment, the implantable medical device 60 includes a heart rate sensor 41 connected to the microprocessor 30. In a preferred embodiment of the present invention, the microprocessor 30 is adapted to check whether the sensed heart rate satisfies at least one predetermined condition, for example, whether the sensed heart rate is within a predetermined lower limit value and a predetermined upper limit value during a predetermined period of time. If the sensed heart rate is found to satisfy the at least one condition, a data collection session is initiated in order to collect hemodynamic sensor signals for use in the creation of a template. Accordingly, the heart level of the patient can be used as a start criteria for the algorithm. The heart rate sensor can be incorporated in the device in accordance with conventional practice within the art.

Figure 2C:
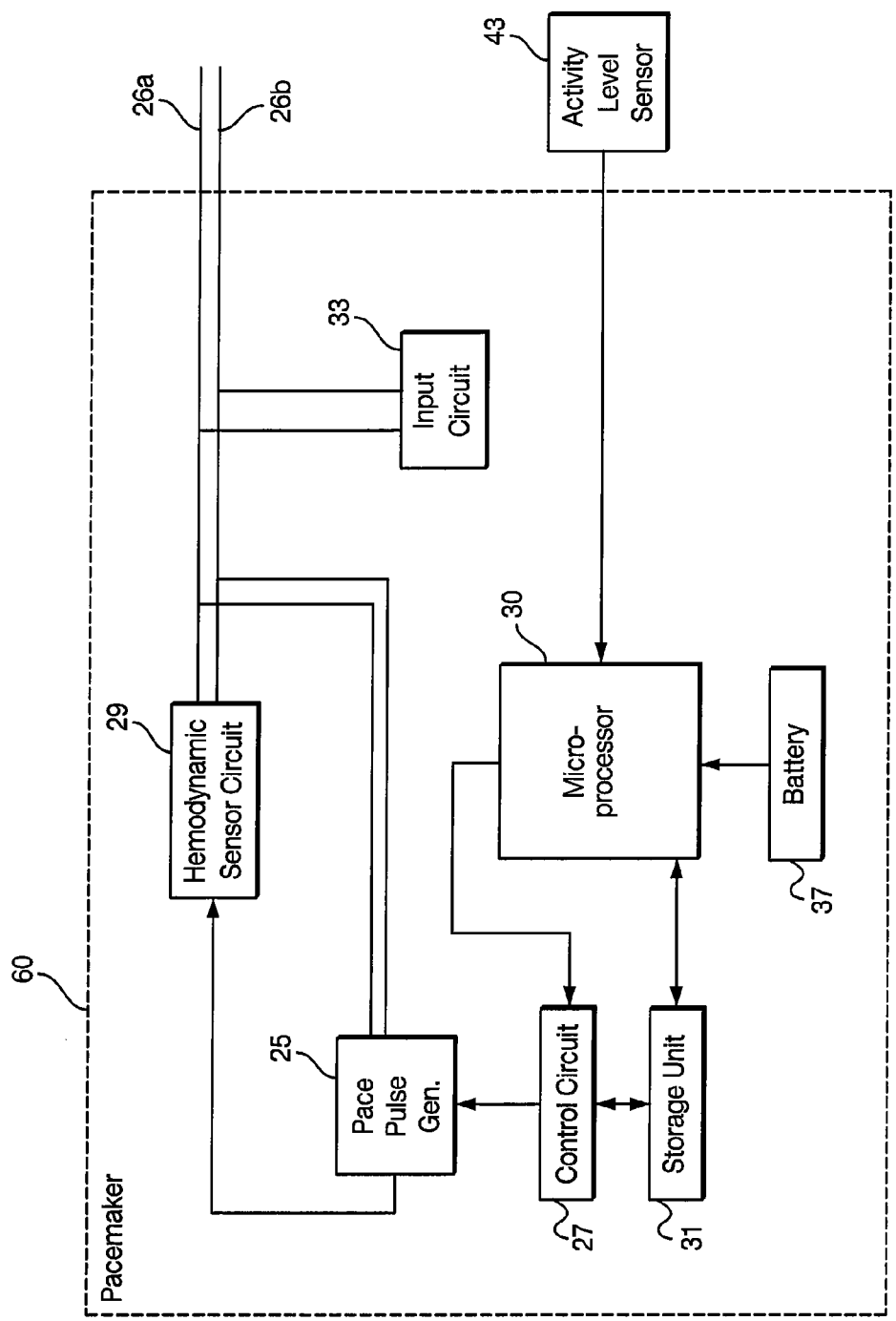
FIG. 2c is block diagram of the primary functional components of a fourth embodiment of an implantable medical device in accordance with the present invention.

Referring now to FIG. 2c, a further embodiment will be discussed. According to this embodiment, the implantable medical device 70 includes an activity level sensor 43 connected to the microprocessor 30. In a preferred embodiment of the present invention, the microprocessor 30 is adapted to check whether the sensed activity level satisfies at least one predetermined condition, for example, whether the sensed activity level is within a predetermined lower limit value and a predetermined upper limit value during a predetermined period of time. If the sensed activity level is found to satisfy the at least one condition, a data collection session is initiated in order to collect hemodynamic sensor signals for use in the creation of a template. Accordingly, the activity level of the patient can be used as a start criteria for the algorithm. The activity level sensor can be incorporated in the device in accordance with conventional practice within the art.

Figure 2D:
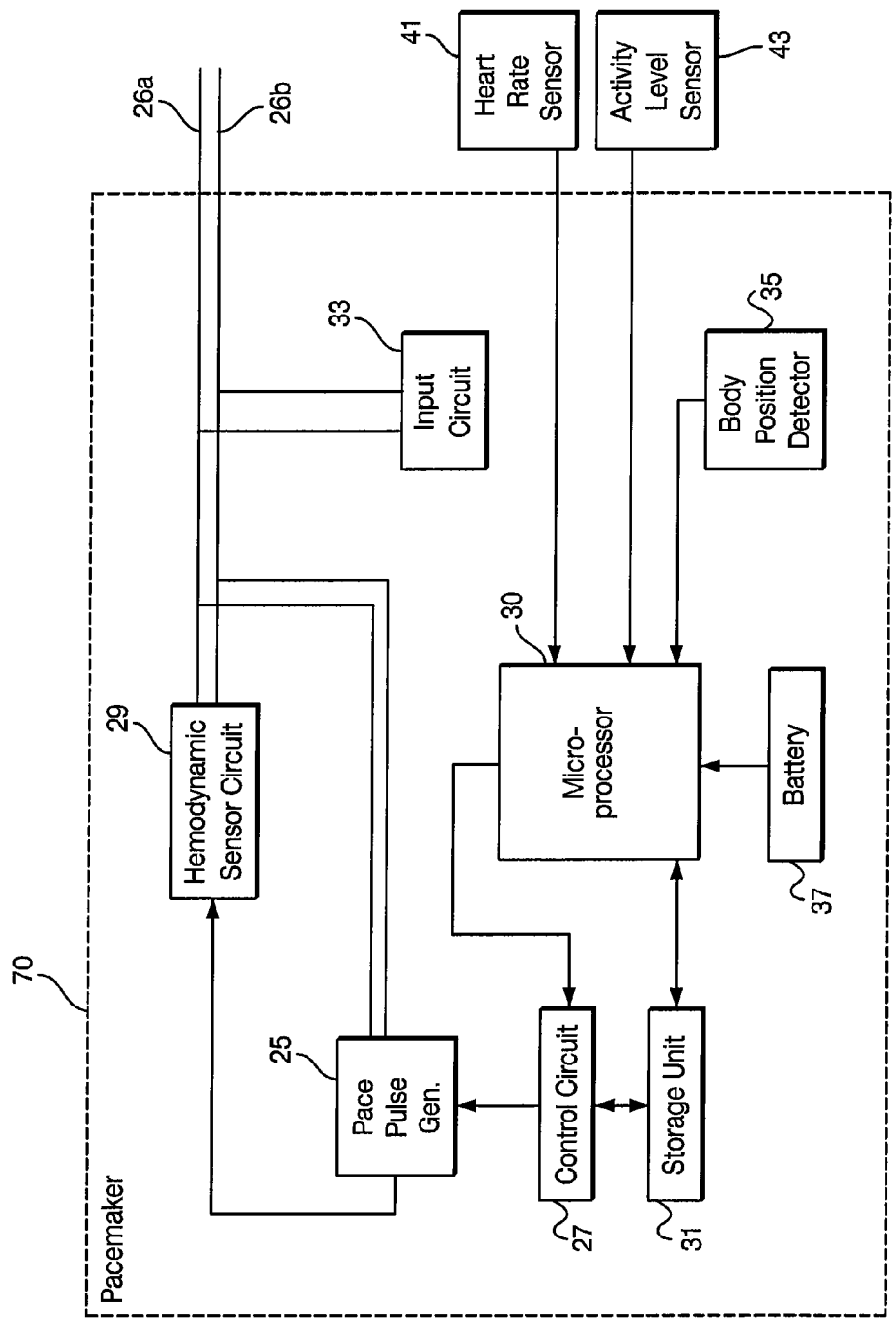
FIG. 2d is block diagram of the primary functional components of a fifth embodiment of an implantable medical device in accordance with the present invention.

As those skilled in the art realizes, one of, some of, or all of the following circuits can be included in the medical device: the position detecting sensor, the heart rate sensor, and the activity level sensor. Consequently, one of, some of, or all of the following parameters can be used as start criteria for the algorithm. In FIG. 2d a medical device comprising the position detecting sensor 35, the heart rate sensor 41, and the activity level sensor 43 is shown. Of course, there are other input parameters that may be used as start criteria, for example, time of day, which also may be combined with any one of, or a combination of, or all of the above-mentioned parameters.

Figure 3:
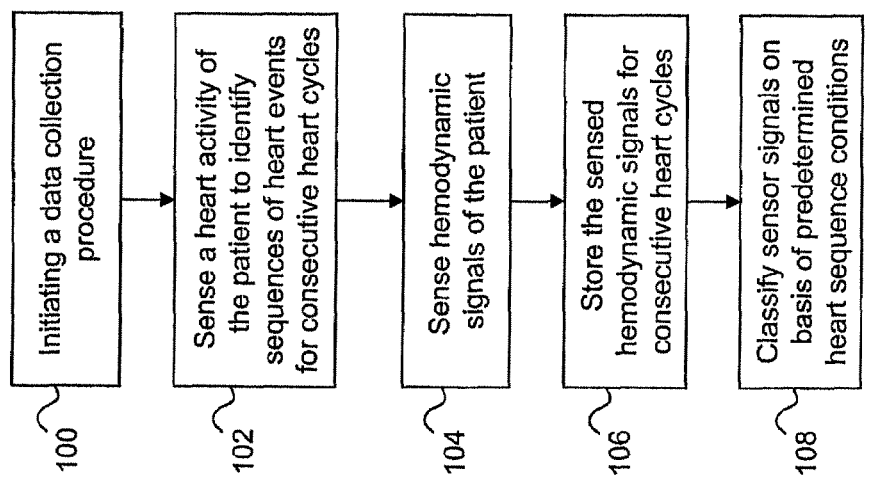
FIG. 3 is a flow chart illustrating the steps in accordance with one embodiment of the method according to the present invention.

Referring now to FIG. 3, a high-level description of the method according to the present invention will be given. At step 100, a data collection session to collect hemodynamic sensor signals for consecutive heart cycles is initiated by the processing unit 30. At step 102, the heart activity of the patient is sensed in order to identify a paced or sensed sequence of events of consecutive heart cycles by means of the input circuit 33. The input circuit 33 is connected to cardiogenic sensors located in the lead 26a and/or 26b adapted to sense events of the heart cycles of the patient, such as a P-wave, a R-wave in the right or left ventricle or a pacing pulse in one of the heart chambers. Accordingly, the paced/sensed sequence of events of the consecutive heart cycles can be identified. Then, at step 104, at least one hemodynamic sensor signal for consecutive heart cycles is sensed using the hemodynamic sensor 29. In one embodiment, the cardiogenic impedance is sensed. Thereafter, at step 106, the sensed hemodynamic sensor signals for the consecutive heart cycles are stored. In this embodiment, the sensed sensor signals for the consecutive cycles are stored in the storage unit 31. At step 108, the sensor signals are classified on basis of predetermined heart sequence conditions. For example, the heart beats can be grouped according to their heart event sequence patterns. Thereby, it can be assured that each heart cycle in a group has substantially the same heart event sequence pattern and that the starting points of the recording of each heart beat is the same event in the heart cycle, e.g. a P-wave, R-wave in the right or left ventricle or a pacing pulse in one of the heart chambers. The processing unit 30 may be pre-programmed with the at least one predetermined heart event sequence condition, for example, a reference sequence. As an example, the sequence condition may in a three-chamber system be A-R1-V2, i.e. an atrial triggered pacing, an intrinsic event in the first chamber and a paced event in the right chamber.

In an embodiment, a predetermined parameter may be identified in or extracted from the consecutive sensor signals, for example, the contractility or the end-diastolic volume. Thereby, it is possible to, for example, trend changes over time of the identified parameter. If the signals are transferred to an external unit (e.g. a programmer), the parameters may identified or extracted in the programmer. In this case, the selected signals are transferred to the external programmer from the implantable medical device via a telemetry link. It is possible to display the parameter over time and to trend, for example, changes of the parameter over time.

The selected sensor signals may be used to create a template. For example, a predetermined number of sensor signals fulfilling the at least one predetermined heart event sequence condition. Thus, a number of signals are collected and sensor signal template is made. The template may be created by averaging the signals into one signal or by median filtering the signals into one, or a combination of the two. As mentioned above, the template may be created in an external programmer. In this case, the selected signals are transferred to the external programmer from the implantable medical device via a telemetry link.

Figure 4:
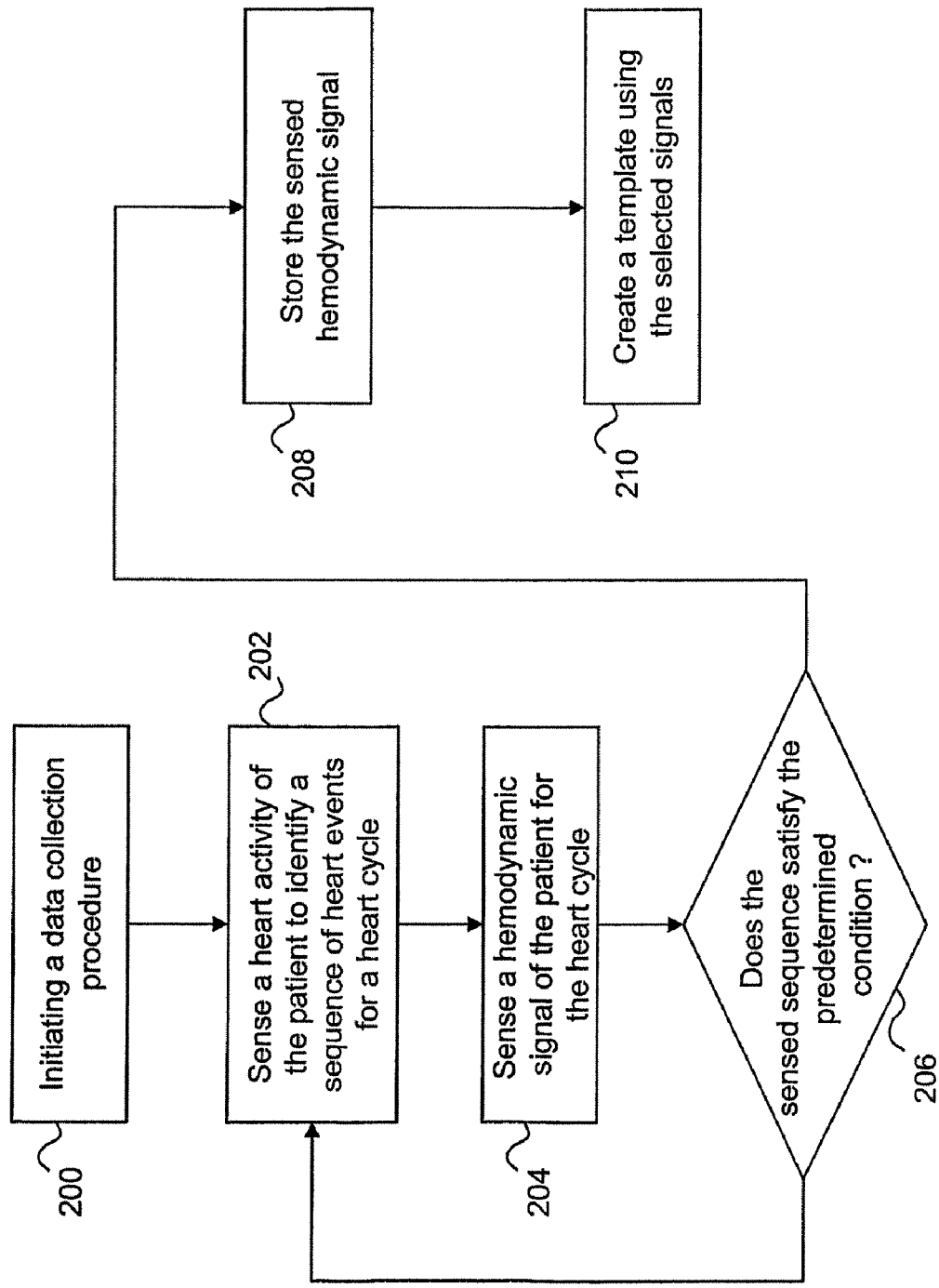
FIG. 4 is a flow chart illustrating the steps in accordance with another embodiment of the method according to the present invention.

With reference now to FIG. 4, an embodiment of the method according to the present invention will be discussed hereinafter. At step 200, a data collection session to collect hemodynamic sensor signals for consecutive heart cycles is initiated by the processing unit 30. At step 202, the heart activity of the patient is sensed in order to identify a paced or sensed sequence of events of a heart cycle by means of the input circuit 33. The input circuit 33 is connected to cardiogenic sensors located in the lead 26a and/or 26b adapted to sense events of the heart cycles of the patient, such as a P-wave, a R-wave in the right or left ventricle or at least one pacing pulse in one of the heart chambers. Accordingly, the paced/sensed sequence of events of the heart cycle can be identified. At step 204, a hemodynamic sensor signal for the heart cycles is sensed using the hemodynamic sensor 29. In one embodiment, the cardiogenic impedance is sensed. Then, at step 206, it is checked whether the paced/sensed sequence of events satisfies at least one predetermined heart event sequence condition are selected. For example, the processing unit 30 may be pre-programmed with the at least one predetermined heart event sequence condition, for example, a reference sequence. As an example, the sequence condition may in a three-chamber system be A-R1-V2, i.e. an atrial triggered pacing, an intrinsic event in the first chamber and paced in the right chamber. That is, the sensed/paced sequence is compared with the reference sequence. If the sensed sequence is found not to correspond to the reference sequence, the algorithm returns to step 202. On the other hand, if the sensed sequence is found to correspond to the reference sequence, the algorithm proceeds to step 208 where the sensed hemodynamic sensor signal is stored. For example, the signal can be stored in the storage 31. In one embodiment this procedure is repeated until a predetermined number of signals have been obtained, for example, 30 signals or, in other words, 30 heart beats. As an alternative, the procedure can be repeated during a predetermined period of time. According to another embodiment, the paced or sensed sequences of heart cycles that is found not to correspond to the reference sequence is counted and the data collection session is aborted if the paced or sensed sequences of heart cycles that is found not to correspond to the reference sequence exceeds a predetermined abortion condition, for example, a predetermined number of sequences.

Subsequently, at step 210, a template using the selected sensor signals may be created. For example, a predetermined number of sensor signals fulfilling the at least one predetermined heart event sequence condition. Thus, a number of signals are collected and sensor signal template is made. The template may be created by averaging the signals into one signal or by median filtering the signals into one, or a combination of the two. As mentioned above, the template may be created in an external programmer. In this case, the selected signals are transferred to the external programmer from the implantable medical device via a telemetry link. Alternatively, a predetermined parameter, such as the contractility or the end-diastolic volume, may be identified in or extracted from the consecutive sensor signals. Thereby, it is possible to, for example, trend changes over time of the identified parameter. If the signals are transferred to an external unit (e.g. a programmer), the parameters may be identified or extracted in the programmer. In this case, the selected signals are transferred to the external programmer from the implantable medical device via a telemetry link. It is possible to display the parameter over time and to trend, for example, changes of the parameter over time.

Figure 5:
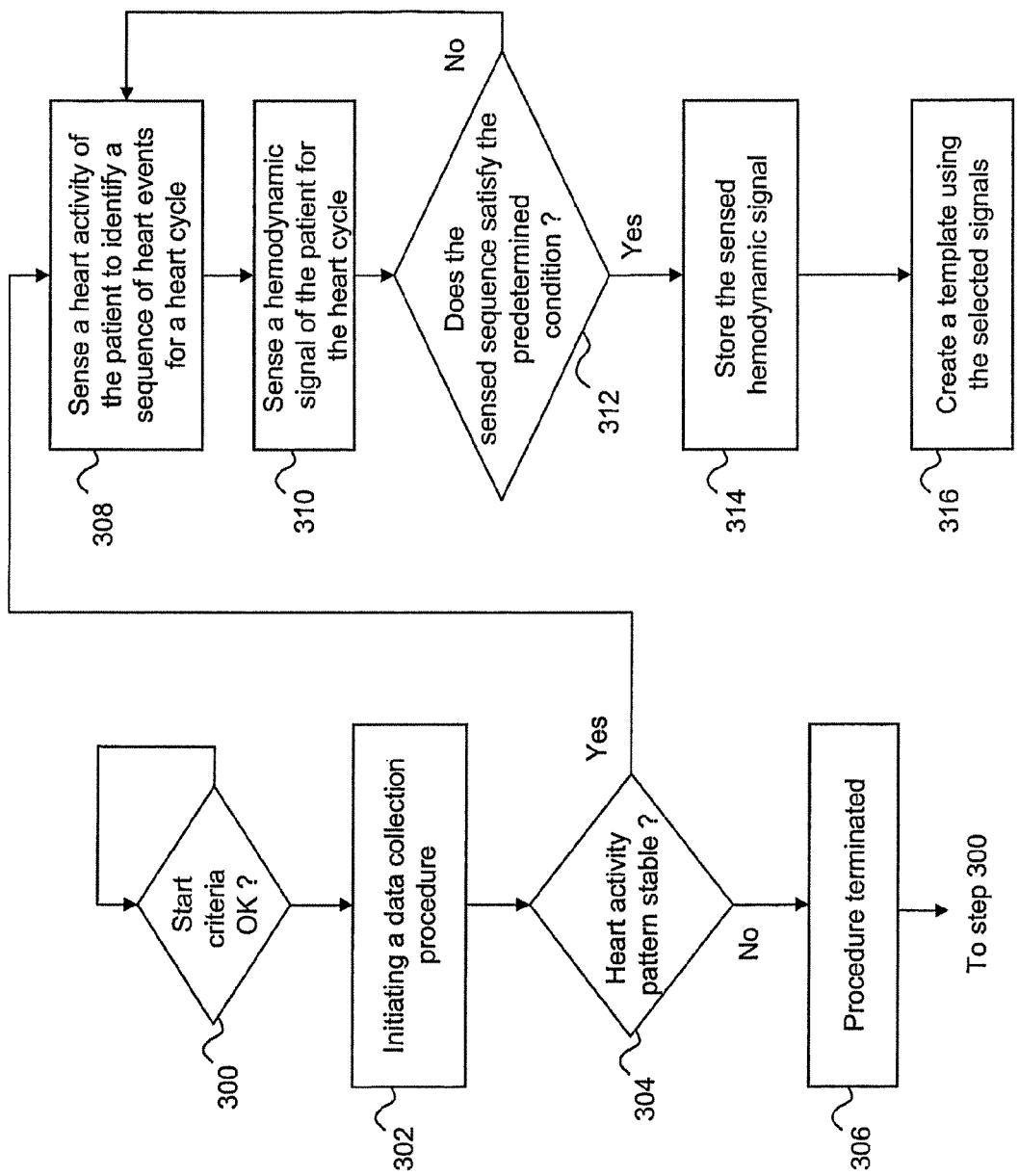
FIG. 5 is a flow chart illustrating the steps in accordance with a further embodiment of the method according to the present invention.

Referring now to FIG. 5, a further embodiment of the method according to the present invention will be described. First, at step 300, a check whether at least one start criteria is fulfilled. According to examples, this at least one start criteria may be whether the patient is in a specific body position, whether a heart rate level of the patient is, for example, within a predetermined interval or below a certain value, or whether an activity level of the patient is within a predetermined interval. If the at least one criteria is fulfilled, the data collecting procedure is initiated in step 302. Then, at step 304, a stability check is performed in order to verify that the heart activity pattern, i.e. the sequences of events, is stable enough for acquiring data for the template. This procedure for checking that the heart activity pattern is stable enough will be described in detail hereinafter. As those skilled will realize, the check whether the contraction pattern of the heart is stable enough may, as an alternative, be performed before the data collection procedure is initiated, i.e. step 304 may be performed before step 302 as will be described below with reference to FIG. 6.

If the heart activity pattern is found not to be stable, the algorithm proceeds to step 306 where the algorithm is terminated. Then, it may return to step 300. On the other hand, if it is found that the heart is working under stable conditions, the algorithm proceeds to step 308, the heart activity of the patient is sensed in order to identify a paced or sensed sequence of events of a heart cycle by means of the input circuit 33. The input circuit 33 is connected to cardiogenic sensors located in the lead 26a and/or 26b adapted to sense events of the heart cycles of the patient, such as a P-wave, a R-wave in the right or left ventricle or a pacing pulse in one of the heart chambers. Accordingly, the paced/sensed sequence of events of the heart cycle can be identified. At step 310, a hemodynamic sensor signal for the heart cycles is sensed using the hemodynamic sensor 29. In one embodiment, the cardiogenic impedance is sensed. Then, at step 312, it is checked whether the paced/sensed sequence of events satisfies at least one predetermined heart event sequence condition are selected. For example, the processing unit 30 may be pre-programmed with the at least one predetermined heart event sequence condition, for example, a reference sequence. As an example, the sequence condition may in a three-chamber system be A-R1-V2, i.e. an atrial triggered pacing, an intrinsic event in the first chamber and paced in the right chamber. That is, the sensed/paced sequence is compared with the reference sequence. If the sensed sequence is found not to correspond to the reference sequence, the algorithm returns to step 308. On the other hand, if the sensed sequence is found to correspond to the reference sequence, the algorithm proceeds to step 314 where the sensed hemodynamic sensor signal is stored. For example, the signal can be stored in the storage 31. In one embodiment this procedure is repeated until a predetermined number of signals have been obtained, for example, 30 signals or, in other words, 30 heart beats. As an alternative, the procedure can be repeated during a predetermined period of time. According to another embodiment, the paced or sensed sequences of heart cycles that is found not to correspond to the reference sequence is counted and the data collection session is aborted if the paced or sensed sequences of heart cycles that is found not to correspond to the reference sequence exceeds a predetermined abortion condition, for example, a predetermined number of sequences.

Subsequently, at step 316, a template using the selected sensor signals may be created. For example, a predetermined number of sensor signals fulfilling the at least one predetermined heart event sequence condition. Thus, a number of signals are collected and sensor signal template is made. The template may be created by averaging the signals into one signal or by median filtering the signals into one, or a combination of the two. As mentioned above, the template may be created in an external programmer. In this case, the selected signals are transferred to the external programmer from the implantable medical device via a telemetry link. Alternatively, a predetermined parameter, such as the contractility or the end-diastolic volume, may be identified in or extracted from the consecutive sensor signals. Thereby, it is possible to, for example, trend changes over time of the identified parameter. If the signals are transferred to an external unit (e.g. a programmer), the parameters may be identified or extracted in the programmer. In this case, the selected signals are transferred to the external programmer from the implantable medical device via a telemetry link. It is possible to display the parameter over time and to trend, for example, changes of the parameter over time.

Figure 6:
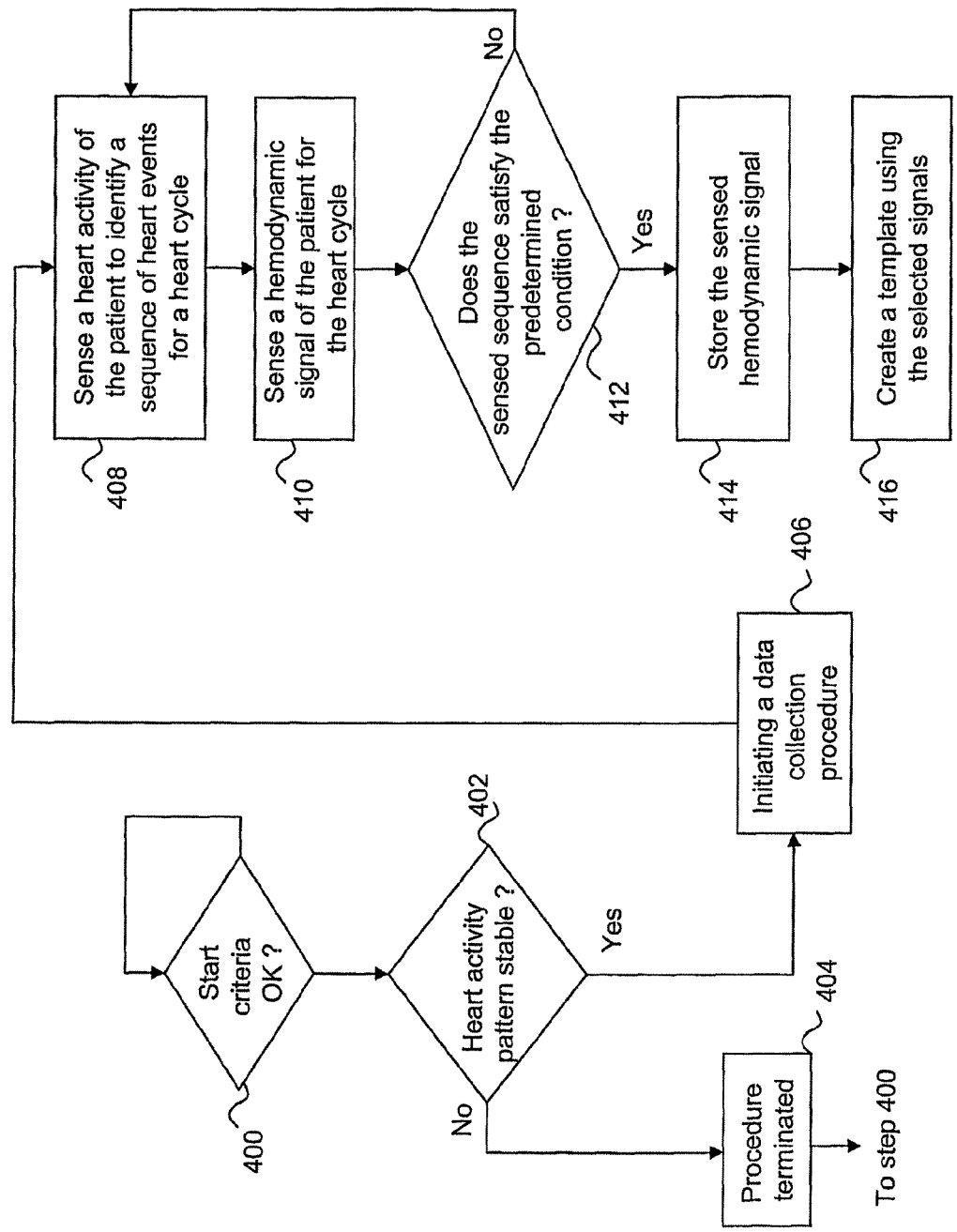
FIG. 6 is a flow chart illustrating the steps in accordance with another embodiment of the method according to the present invention.

With reference to FIG. 6, yet another embodiment of the method according to the present invention will be described. First, at step 400, a check whether at least one start criteria is fulfilled. According to examples, this at least one start criteria may be whether the patient is in a specific body position, whether a heart rate level of the patient is, for example, within a predetermined interval or below a certain value, or whether an activity level of the patient is within a predetermined interval. If the at least one criteria is fulfilled, the procedure proceeds to step 402 where a stability check is performed. Then, at step 402, a stability check is performed in order to verify that the heart activity pattern, i.e. the sequences of events, is stable enough for acquiring data for the template. This procedure for checking that the heart activity pattern is stable enough will be described in detail hereinafter. If the heart activity pattern is found not to be stable, the algorithm proceeds to step 404 where the algorithm is terminated. Then, it may return to step 400. On the other hand, if it is found that the heart is working under stable conditions, the algorithm proceeds to step 406 where a data collection procedure session is initiated. Then, at step 408, the heart activity of the patient is sensed in order to identify a paced or sensed sequence of events of a heart cycle by means of the input circuit 33. The input circuit 33 is connected to cardiogenic sensors located in the lead 26a and/or 26b adapted to sense events of the heart cycles of the patient, such as a P-wave, a R-wave in the right or left ventricle or a pacing pulse in one of the heart chambers. Accordingly, the paced/sensed sequence of events of the heart cycle can be identified. At step 410, a hemodynamic sensor signal for the heart cycles is sensed using the hemodynamic sensor 29. In one embodiment, the cardiogenic impedance is sensed. Then, at step 412, it is checked whether the paced/sensed sequence of events satisfies at least one predetermined heart event sequence condition are selected. For example, the processing unit 30 may be pre-programmed with the at least one predetermined heart event sequence condition, for example, a reference sequence. As an example, the sequence condition may in a three-chamber system be A-R1-V2. That is, the sensed/paced sequence is compared with the reference sequence. If the sensed sequence is found not to correspond to the reference sequence, the algorithm returns to step 408. On the other hand, if the sensed sequence is found to correspond to the reference sequence, the algorithm proceeds to step 414 where the sensed hemodynamic sensor signal is stored. For example, the signal can be stored in the storage 31. In one embodiment this procedure is repeated until a predetermined number of signals have been obtained, for example, 30 signals or, in other words, 30 heart beats. As an alternative, the procedure can be repeated during a predetermined period of time. According to another embodiment, the paced or sensed sequences of heart cycles that is found not to correspond to the reference sequence is counted and the data collection session is aborted if the paced or sensed sequences of heart cycles that is found not to correspond to the reference sequence exceeds a predetermined abortion condition, for example, a predetermined number of sequences.

Subsequently, at step 416, a template using the selected sensor signals may be created. For example, a predetermined number of sensor signals fulfilling the at least one predetermined heart event sequence condition. Thus, a number of signals are collected and sensor signal template is made. The template may be created by averaging the signals into one signal or by median filtering the signals into one, or a combination of the two. As mentioned above, the template may be created in an external programmer. In this case, the selected signals are transferred to the external programmer from the implantable medical device via a telemetry link. Alternatively, a predetermined parameter, such as the contractility or the end-diastolic volume, may be identified in or extracted from the consecutive sensor signals. Thereby, it is possible to, for example, trend changes over time of the identified parameter. If the signals are transferred to an external unit (e.g. a programmer), the parameters may be identified or extracted in the programmer. In this case, the selected signals are transferred to the external programmer from the implantable medical device via a telemetry link. It is possible to display the parameter over time and to trend, for example, changes of the parameter over time.

Now embodiments of the stability check procedure will be described. As indicated above, the algorithm verifies that the cardiac contraction pattern is stable enough to collect data for the cardiogenic sensor template in step 304 in FIG. 5 and 402 in FIG. 6. According to a first embodiment, the algorithm is programmed to collect data at a specific predetermined paced/sensed sequence, for example, A-R1-V1, i.e. a reference sequence. Consecutive heart cycles during a predetermined interval are sensed or monitored and each paced/sensed sequence is compared with the reference sequence to check whether it correspond to the reference sequence or not. If a predetermined percentage of the sensed/paced sequences corresponds to the reference sequence, the algorithm will determine the contraction patter in stable enough for performing a data collection procedure. For example, the predetermined percentage may be set to 75% and the reference sequence may be A-R1-V1. If twelve heart beats occur during the predetermined interval, the contraction pattern will be determined to be stable if nine or more of the paced/sensed sequences are A-R1-V1.

In a second embodiment, the algorithm is set to collect data at any paced/sensed sequence. In this case, the algorithm counts the prevalence of the possible different sequences during the predetermined interval. The sequence that is found to be most prevalent is used as the reference sequence. To assure that the contraction pattern of the heart is stable enough, a minimal level of the prevalence of the paced/sensed sequence is set. For example, the following sequences were identified during a predetermined interval:

A-R1-R2=1
A-R1-V2=9
P-R1-VL=1
A-V1-V2=1
P-R1-R2=0

In this case, the sequence A-R1-V2 would be selected for use during the sensor signal template collection. The percentage prevalence also satisfies the minimum requirements, i.e. more than 75%.

An alternative is to count the prevalence of atrial, right and left ventricular sensed/paced events and determine the reference sequence based on that. In the above example, the following events would be identified:
A=11
P=1
R1=11
V1=1
R2=1
V2=11

In this case, the sequence A-R1-V2 would also be selected for use during the sensor signal template collection.

Although an exemplary embodiment of the present invention has been shown and described, it will be apparent to those having ordinary skill in the art that a number of changes, modifications, or alterations to the inventions as described herein may be made. Thus, it is to be understood that the above description of the invention and the accompanying drawings is to be regarded as a non-limiting example thereof and that the scope of protection is defined by the appended patent claims.

We claim as our invention:

1. A method for classifying hemodynamic sensor signals using an implantable medical device being connectable to a patient, said method comprising:
performing a data collection session for collecting hemodynamic sensor signals for consecutive heart cycles including: sensing a heart activity of a patient; identifying a paced or sensed sequence of atrial and ventricular events of a heart cycle wherein the sequence corresponds to the order in which the paced or sensed atrial and ventricular events occurred; sensing hemodynamic sensor signals for consecutive heart cycles; storing said sensed hemodynamic sensor signals for consecutive heart cycles; and
classifying sensed sensor signals on basis of at least one predetermined heart event sequence condition.

2. The method according to claim 1, wherein the step of classifying comprises the step of selecting sensor signals for heart cycles having paced or sensed sequences of events that satisfies said at least one predetermined heart event sequence condition.

3. The method according to claim 1, wherein said at least one predetermined heart event sequence condition includes a reference sequence.

4. The method according to claim 1, further comprising the step of creating a template using said selected sensor signals.

5. The method according to claim 4, wherein said step of selecting is performed in said data collection session and comprises the steps of:
checking whether the paced or sensed sequence of events of a heart cycle corresponds to said reference sequence;
if said paced or sensed sequence of said heart cycle is found to correspond to said reference sequence, storing the sensed hemodynamic sensor signal for said heart cycle for use in said template, and
wherein said template is created using said stored sensor signals.

6. The method according to claim 5, further comprising the steps of:
determining whether a series of paced or sensed sequences of events is stable; and
if said series is found to be stable, initiating said data collection session in order to collect hemodynamic sensor signal for creating said template.

7. The method according to claim 6, wherein the step of determining whether a series of paced or sensed sequences of events is stable comprises the steps of:
sensing a heart activity of a patient during a predetermined period of time;
checking whether a prevalence of a paced or sensed sequence of events of consecutive heart cycles that corresponds to said reference sequence satisfies at least one predetermined condition; and
if said at least one predetermined condition is found to be satisfied, determining that said series of paced or sensed sequences of events of said patient is stable.

8. The method according to claim 7, wherein said reference sequence is a predetermined sequence of paced or sensed events and wherein the step of checking whether a prevalence of a paced or sensed sequence of events of consecutive heart cycles that corresponds to said reference sequence satisfies at least one predetermined condition comprises the step of:
checking whether at least a predetermined percentage of the sequences of events of the heart cycles occurring during said predetermined period of time correspond to said reference sequence.

9. The method according to claim 7, wherein the step of checking whether a prevalence of a paced or sensed sequence of events of consecutive heart cycles that corresponds to said reference sequence satisfies at least one predetermined condition comprises the steps of:
counting the prevalence of different sequences of events of the heart cycles occurring during said predetermined period of time; and
using the most prevalent sequence as said reference sequence.

10. The method according to claim 9, further comprising the step of:
checking whether said most prevalent sequence exceeds a minimum level of prevalence of sequences.

11. The method according to claim 4, wherein the step of creating a template using a predetermined number of sensor signals comprises the step of:
creating said template by averaging the hemodynamic sensor signals.

12. The method according to claim 4, wherein the step of creating a template using a predetermined number of sensor signals comprises the step of:
creating said template by median filtering the hemodynamic sensor signals.

13. The method according to claim 4, wherein the step of creating a template using a predetermined number of sensor signals comprises the step of:
creating said template by weighting the hemodynamic sensor signal for different heart cycles with predetermined weights.

14. The method according to claim 4, wherein said template is created by means of a predetermined number of sensor signals.

15. The method according to claim 5, further comprising the step of:
counting paced or sensed sequences of heart cycles that is found not to correspond to said reference sequence; and aborting said data collection session if the paced or sensed sequences of heart cycles that is found not to correspond to said reference sequence exceeds a predetermined abortion condition.

16. The method according to claim 1, further comprising the step of:
aborting said data collection session if a predetermined period of time has lapsed.

17. The method according to claim 1, further comprising the steps of identifying at least one predetermined parameter in each of said selected sensor signals.

18. The method according to claim 1, wherein the step of sensing hemodynamic sensor signals for consecutive heart cycles comprises the step of:
sensing the cardiac component of an electrical bio-impedance of said patient.

19. The method according to claim 18, wherein the step of sensing the cardiac component of the electrical bio-impedance comprises the steps of:
applying an excitation current pulse between at least a first electrode and at least a second electrode of said electrode configuration;
sensing the impedance in tissues between said electrodes to the excitation current pulse; and
extracting the cardiac component of said sensed impedance.

20. The method according to claim 1, wherein the step of sensing hemodynamic sensor signals for consecutive heart cycles comprises the step of:
sensing a blood pressure of said patient.

21. The method according to claim 1, wherein the step of sensing hemodynamic sensor signals for consecutive heart cycles comprises the step of:
sensing a blood flow of said patient.

22. The method according to claim 1, further comprising the steps of:
sensing a heart rate of said patient;
checking whether said sensed heart rate satisfies at least one predetermined conditions; and
if said sensed heart rate is found to satisfy said at least one condition, initiating said data collection session.

23. The method according to claim 1, further comprising the steps of:
sensing an activity level of said patient;
checking whether said sensed activity level satisfies at least one predetermined condition; and
if said sensed activity level is found to satisfy said at least one condition, initiating said data collection session.

24. A method for classifying hemodynamic sensor signals using an implantable medical device being connectable to a patient characterized by the steps of:
performing a data collection session for collecting hemodynamic sensor signals for consecutive heart cycles including: sensing a heart activity of a patient in order to identify a paced or sensed sequence of events of a heart cycle; sensing hemodynamic sensor signals for consecutive heart cycles; storing said sensed hemodynamic sensor signals for consecutive heart cycles;
classifying sensed sensor signals on the basis of at least one predetermined heart event sequence condition;
detecting at least one body position of said patient; and
initiating said data collection session when said patient is in said at least one body position.

25. A method for classifying hemodynamic sensor signals using an implantable medical device being connectable to a patient characterized by the steps of:
performing a data collection session for collecting hemodynamic sensor signals for consecutive heart cycles including: sensing a heart activity of a patient in order to identify a paced or sensed sequence of events of a heart cycle; sensing hemodynamic sensor signals for consecutive heart cycles; storing said sensed hemodynamic sensor signals for consecutive heart cycles;
classifying sensed sensor signals on the basis of at least one predetermined heart event sequence condition;
sensing a breath rate of said patient;
checking whether said sensed breath rate satisfies at least one predetermined condition; and
if said sensed breath rate is found to satisfy said at least one condition, initiating said data collection session.

26. A medical device for classifying hemodynamic sensor signals being connectable to a patient comprising:
a heart activity sensor configured to sense a heart activity of a patient;
a hemodynamic sensor configured to sense hemodynamic signals for consecutive heart cycles;
a storage device in which said sensed hemodynamic sensor signals for consecutive heart cycles are stored;
a processing unit configured to:
perform a data collection session for collecting hemodynamic sensor signals for consecutive heart cycles including: to obtain paced or sensed sequences of atrial and ventricular events of heart cycles from said heart activity sensor, wherein the sequence corresponds to the order in which the paced or sensed atrial and ventricular events occurred; to trigger said hemodynamic sensor to initiate a sensing session in order to sense hemodynamic sensor signals for consecutive heart cycles; and to store said sensed hemodynamic sensor signals for consecutive heart cycles in said storage; and to classify sensed sensor signals on basis of at least one predetermined heart event sequence condition.

27. The device according to claim 26, wherein said processing unit is configured to select sensor signals for heart cycles having paced or sensed sequences of events that satisfies said at least one predetermined heart event sequence condition.

28. The device according to claim 27, wherein said at least one predetermined heart event sequence condition includes a reference sequence.

29. The device according to claim 27, wherein said processing unit is configured to create a template using said selected sensor signals.

30. The device according to claim 29, wherein said processing unit is further configured to:
check whether the paced or sensed sequence of events of a heart cycle corresponds to said reference sequence;
if said paced or sensed sequence of said heart cycle is found to correspond to said reference sequence, store the sensed hemodynamic sensor signal for said heart cycle for use in said template in said storage, and
create said template using said stored sensor signals.

31. The device according to claim 30, wherein said processing unit is further configured to:
determine whether a series of paced or sensed sequences of events is stable; and
if said series is found to be stable, initiate said data collection session in order to collect hemodynamic sensor signal for creating said template.

32. The device according to claim 31, wherein said processing unit is further configured to:

obtain paced or sensed sequences of events of heart cycles from said heart activity sensor during a predetermined period of time;

check whether a prevalence of a paced or sensed sequence of events of consecutive heart cycles that corresponds to said reference sequence satisfies at least one predetermined condition; and if said at least one predetermined condition is found to be satisfied, determine that said series of paced or sensed sequences of events of said patient is stable.

33. The device according to claim 32, wherein said reference sequence is a predetermined sequence of paced or sensed events and wherein said processing unit is further configured to:

check whether at least a predetermined percentage of the sequences of events of the heart cycles occurring during said predetermined period of time correspond to said reference sequence.

34. The device according to claim 32, wherein said processing unit is further configured to:

count the prevalence of different sequences of events of the heart cycles occurring during said predetermined period of time; and use the most prevalent sequence as said reference sequence.

35. The device according to claim 34, wherein said processing unit is further configured to:

check whether said most prevalent sequence exceeds a minimum level of prevalence of sequences.

36. The device according to claim 30, wherein said processing unit is further configured to:

count paced or sensed sequences of heart cycles that is found not to correspond to said reference sequence; and abort said data collection session if the paced or sensed sequences of heart cycles that is found not to correspond to said reference sequence exceeds a predetermined abortion condition.

37. The device according to claim 27, further wherein said processing unit is further configured to:

abort said data collection session if a predetermined period of time has lapsed.

38. The device according to claim 27, wherein said processing unit is configured to identify at least one predetermined parameter in each of said selected sensor signals.

39. The device according to claim 27, wherein the hemodynamic sensor is an impedance sensor configured to sense the cardiac component of an electrical bio-impedance of said patient.

40. The device according to claim 39, wherein the impedance sensor is configured to sense the cardiac component of an electrical bio-impedance of said patient and wherein said device comprises:

a pacing arrangement configured to apply an excitation current pulse between at least a first electrode and at least a second electrode;

a sensing arrangement that senses the impedance in tissues between said electrodes to the excitation current pulse; and an extraction unit that extracts the cardiac component of said sensed impedance.

41. The device according to claim 27, wherein the hemodynamic sensor is a blood pressure sensor configured to sense a blood pressure of said patient.

42. The device according to claim 27, wherein the hemodynamic sensor is a blood flow sensor adapted to sense a blood flow of said patient.

43. The device according to claim 29, wherein said template is formed by a predetermined number of sensor signals.

44. The device according to claim 27, further comprising a heart rate sensor configured to sense a heart rate of said patient; and wherein said processing unit is configured to:

check whether said sensed heart rate satisfies at least one predetermined conditions; and if said sensed heart rate is found to satisfy said at least one condition, initiate said data collection session.

45. The device according to claim 27, further comprising an activity sensor configured to sense an activity level of said patient; and wherein said processing unit is configured to:

check whether said sensed activity level satisfies at least one predetermined condition; and if said sensed activity level is found to satisfy said at least one condition, initiate said data collection session.

46. The device according to claim 29, wherein said processing unit is configured to:

create said template by averaging the hemodynamic sensor signals.

47. The device according to claim 29, wherein said processing unit is configured to:

form said template by median filtering the hemodynamic sensor signals.

48. The device according to claim 29, wherein said processing unit is configured to:

form said template by weighting the hemodynamic sensor signal for different heart cycles with predetermined weights.

49. A medical device for classifying hemodynamic sensor signals being connectable to a patient comprising:

a heart activity sensor configured to sense a heart activity of a patient;

a hemodynamic sensor configured to sense hemodynamic signals for consecutive heart cycles;

a storage device in which said sensed hemodynamic sensor signals for consecutive heart cycles are stored;

a processing unit configured to:

perform a data collection session for collecting hemodynamic sensor signals for consecutive heart cycles including: to obtain paced or sensed sequences of events of heart cycles from said heart activity sensor; to trigger said hemodynamic sensor to initiate a sensing session in order to sense hemodynamic sensor signals for consecutive heart cycles; and to store said sensed hemodynamic sensor signals for consecutive heart cycles in said storage; and to classify sensed sensor signals on basis of at least one predetermined heart event sequence condition; and a position detecting sensor configured to detect at least one body position of said patient; and wherein said processing unit is configured to:

initiate said data collection session when said patient is in said at least one body position.

50. A medical device for classifying hemodynamic sensor signals being connectable to a patient comprising:

a heart activity sensor configured to sense a heart activity of a patient;

a hemodynamic sensor configured to sense hemodynamic signals for consecutive heart cycles;

a storage device in which said sensed hemodynamic sensor signals for consecutive heart cycles are stored;

a processing unit configured to:
   perform a data collection session for collecting hemodynamic sensor signals for consecutive heart cycles including: to obtain paced or sensed sequences of events of heart cycles from said heart activity sensor; to trigger said hemodynamic sensor to initiate a sensing session in order to sense hemodynamic sensor signals for consecutive heart cycles; and to store said sensed hemodynamic sensor signals for consecutive heart cycles in said storage; and to classify sensed sensor signals on basis of at least one predetermined heart event sequence condition; and
a breath rate sensor configured to sense a breath rate of said patient; and wherein said processing unit is configured to:
   check whether said sensed breath rate satisfies at least one predetermined condition; and
   if said sensed breath rate is found to satisfy said at least one condition, initiate said data collection session.

* * * * *